US005484896A

United States Patent [19]
Naieni et al.

[11] Patent Number: 5,484,896
[45] Date of Patent: Jan. 16, 1996

[54] ESTERIFIED HIGH LIGNIN CONTENT CELLULOSIC FIBERS

[75] Inventors: Shahrokh A. Naieni; Carlisle M. Herron, both of Cincinnati, Ohio; Thomas R. Hanser, Taylor Mill, Ky.

[73] Assignee: The Proctor & Gamble Company, Cincinnati, Ohio

[21] Appl. No.: 217,465

[22] Filed: Mar. 24, 1994

[51] Int. Cl.[6] .................... C07G 1/00; C08L 97/00; C08L 97/02; A61F 13/15
[52] U.S. Cl. .................... 530/504; 530/507; 536/63; 602/49; 604/358; 604/374; 604/375; 604/376
[58] Field of Search ................ 536/63; 530/504, 530/507; 602/49; 604/358, 374, 375, 376

[56] References Cited

U.S. PATENT DOCUMENTS

| | | |
|---|---|---|
| 2,971,815 | 2/1961 | Bullock et al. . |
| 3,294,779 | 12/1966 | Bullock et al. . |
| 3,472,839 | 10/1969 | Tesoro . |
| 3,526,048 | 9/1970 | Rowland et al. ............ 38/144 |
| 3,776,692 | 12/1973 | Franklin et al. ............ 8/181 |
| 3,854,866 | 12/1974 | Franklin et al. . |
| 3,901,236 | 8/1975 | Assarsson et al. ............ 128/284 |
| 3,971,379 | 7/1976 | Chatterjee . |
| 4,820,307 | 4/1989 | Welch et al. ............ 8/120 |
| 4,822,453 | 4/1989 | Dean et al. ............ 162/157.6 |
| 4,853,086 | 8/1989 | Graef ............ 162/157.6 |
| 4,888,093 | 12/1989 | Dean et al. ............ 162/157.6 |
| 4,889,595 | 12/1989 | Herron et al. ............ 162/157.6 |
| 4,889,596 | 12/1989 | Schoggen et al. ............ 162/157.6 |
| 4,889,597 | 12/1989 | Bourbon et al. ............ 162/157.6 |
| 4,898,642 | 2/1990 | Moore et al. ............ 162/157.6 |
| 5,137,537 | 8/1992 | Herron et al. ............ 8/120 |
| 5,183,707 | 2/1993 | Herron et al. ............ 428/364 |
| 5,190,563 | 3/1993 | Herron et al. ............ 8/120 |

OTHER PUBLICATIONS

Clark Welch "Tetracarboxylic Acids as Formaldehyde-Free Durable Press Finishing Agents", *Textile Research Journal*, 58, No. 8, pp. 480–486 (Aug. 1988).
Gagliardi and Shippee, "Crosslinking of Cellulose with Polycarboxylic Acids", *American Dyestuff Reporter*, pp. 300–303 (Apr. 15, 1963).

*Primary Examiner*—Nathan M. Nutter
*Attorney, Agent, or Firm*—Harness, Dickey & Pierce

[57] ABSTRACT

Individualized, esterified high lignin content cellulosic fibers containing intrafiber $C_2$–$C_9$ polycarboxylic acid ester perform unexpectedly better in absorbent applications than lower lignin content esterified fibers from the same furnish.

12 Claims, No Drawings

5,484,896

ESTERIFIED HIGH LIGNIN CONTENT CELLULOSIC FIBERS

TECHNICAL FIELD

This invention is directed to modifying high lignin content cellulosic fibers for use in absorbent structures.

BACKGROUND OF THE INVENTION

High lignin cellulosic fibers have the advantages of being inexpensive and relatively chemical-free compared to fibers from bleached Kraft pulp. However, they are not useful as major constituents in absorbent structures, e.g., diapers and catamenial products, because of their high hydrophobicity due to the presence of such a large amount of hydrophobic lignin.

SUMMARY OF THE INVENTION

It has been discovered herein that polycarboxylic acid esterified high lignin content fibers have unexpectedly better wet resiliency than and comparable dry resiliency and drip capacity compared to esterified lower lignin content (Kraft) fibers from the same furnish.

One embodiment herein is directed to individualized esterified high lignin content cellulosic fibers containing from about 0.5 to about 8% by weight, on a citric acid basis applied on a dry fiber basis, of reacted $C_2$–$C_9$ polycarboxylic acid and having a water retention value ranging from about 65 to 125. Normally, these individualized esterified high lignin content cellulosic fibers have a dry resiliency defined by a 5K density ranging from about 0.08 to 0.22 gm/cc, a wet resiliency defined by a wet compressibility ranging from 6.0 to 11.0 cc/gm, and a drip capacity ranging from 7.0 to 16.0 g/g. In this embodiment, the individualized esterified high lignin content cellulosic fibers in application often contain from about 3% to about 4.5% by weight, on a citric acid basis applied on a dry fiber basis, of reacted $C_2$–$C_9$ polycarboxylic acid and have a water retention value ranging from about 75 to 110, a dry resiliency defined by a 5K density ranging from about 0.10 to 0.18 gm/cc, a wet resiliency defined by a wet compressibility ranging from about 7.2 to 8.75 cc/gm and a drip capacity ranging from about 8.0 to 12.5 g/g. Preferably, the $C_2$–$C_9$ polycarboxylic acid is citric acid.

A second embodiment herein is directed to an absorbent structure comprising individualized esterified high lignin content cellulosic fibers containing from about 0.5 to about 8% by weight, on a citric acid basis applied on a dry fiber basis, of reacted $C_2$–$C_9$ polycarboxylic acid and having a water retention value ranging from 65 to 125, a dry resiliency defined by a 5K density ranging from about 0.08 to 0.22 gm/cc, a wet resiliency defined by a wet compressibility ranging from 6.0 to 11.0 cc/gm and a drip capacity ranging from about 7.0 to 16.0 g/g. In this embodiment, the individualized esterified high lignin content cellulosic fibers in application often contain from about 3% to about 4.5% by weight, on a citric acid basis applied on a dry fiber basis, of reacted $C_2$–$C_9$ polycarboxylic acid and have a water retention value ranging from about 75 to 110, a dry resiliency defined by a 5K density ranging from about 0.10 to 0.18 gm/cc, a wet resiliency defined by a wet compressibility ranging from about 7.2 to 8.75 cc/gm and a drip capacity ranging from about 8.0 to 12.5 g/g. Preferably, the $C_2$–$C_9$ polycarboxylic acid is citric acid. The individualized esterified high lignin content cellulosic fibers provide absorbent structures of increased dry resiliency manifesting increased potential for absorption in use situations (i.e., after compression), increased wet resiliency manifesting increased capacity for absorption after wetness occurs (e.g., to provide a crotch area for a diaper which rapidly distributes urine under load to other areas of the diaper instead of leaking), and increased drip capacity manifesting increased capacity for absorption and increased absorbency rate, compared to high lignin content cellulosic fibers which are not esterified.

The term "esterified" used in defining the fibers in the above embodiments denotes intrafiber $C_2$–$C_9$ polycarboxylic acid ester moieties. The ester moieties are the polycarboxylic acid residues present in the form of ester crosslinking bonds provided by reaction of carboxyl groups of polycarboxylic acid reacting with hydroxyls in adjacent cellulose molecules, present as a result of reaction of carboxyl groups of polycarboxylic acid with hydroxyls on the same cellulose molecule, and present as a result of reaction of a single carboxyl group of a polycarboxylic acid reacting with cellulose hydroxyl and present as a result of one or more carboxyl groups of polycarboxylic acid reacting with lignin hydroxyl. Free carboxyls provided in the reactions increase hydrophilicity.

The term "intrafiber" means that a polycarboxylic acid molecule is reacted only with a molecule or molecules of a single fiber rather than interfiber, i.e., between molecules of separate fibers. The esterification crosslinking reactions between cellulose molecules impart stiffness to the fibers.

The intrafiber reactions provide stiffness to the fibers without imparting rigidity.

The term "individualized esterified fibers" is used herein to mean that crosslinking esterifications are primarily intrafiber rather than interfiber.

The term "high lignin content" is used herein to mean 10 to 25% by weight lignin, on a dry basis.

The term "citric acid basis" is used herein to mean the weight of citric acid providing the same number of reacting carboxyl groups as are provided by the polycarboxylic acid actually used, with the reacting carboxyl groups being the reactive carboxyl groups less one per molecule. The term "reactive carboxyl groups" is defined later.

The term "applied on a dry fiber basis" means that the percentage is established by a ratio wherein the denominator is the weight of cellulosic fibers present if they were dry (i.e., no moisture content).

The weight of reacted polycarboxylic acid contained in the fibers of the instant invention is determined by the following procedure: First a sample of the esterified fibers is washed with sufficient hot water to remove any unreacted esterifying agent and catalysts. Next, the fibers are dried to equilibrium moisture content. Then, the free carboxyl group content is determined essentially in accordance with T.A.P.P.I. method T237 OS-77. The weight of reacted polycarboxylic acid is then calculated based on the assumptions that one carboxyl group is left unreacted in each molecule of polycarboxylic acid, that the fibers before reaction have a carboxyl content of 30 meq/kg and that no new carboxyls are generated on cellulose molecules during the esterification apart from the free carboxyls on ester moieties. The result is converted to a citric acid basis by utilizing the relationship set forth in the above paragraph.

The "water retention values" (referred to in the Examples herein as WRV) set forth herein are determined herein by the following procedure: A sample of about 0.3 g to about 0.4 g of fibers (i.e., about a 0.3 g to about a 0.4 g portion of the fibers for which water retention values are being determined) is soaked in a covered container with about 100 ml distilled or deionized water at room temperature for between about 15 and about 20 hours. The soaked fibers are collected on a filter and transferred to an 80-mesh wire basket supported about 1½ inches above a 60-mesh screened bottom of a centrifuge tube. The tube is covered with a plastic cover and the sample is centrifuged at a relative centrifuge force of 1500 to 1700 gravities for 19 to 21 minutes. The centrifuged fibers are then removed from the basket and weighed. The weighed fibers are dried to a constant weight at 105° C. and reweighed. The water retention value (WRV) is calculated as follows:

$$WRV = \frac{(W-D)}{D} \times 100$$

where, W=wet weight of the centrifuged fibers; D=dry weight of the fibers; and W-D=weight of absorbed water.

The term "dry resiliency" is used herein to refer to the ability of a structure made from the fibers herein to expand upon release of compressional force applied while the fibers are in substantially dry condition. Dry resiliency defined by a density after pressing is a measure of fiber stiffness and is determined herein in the 5K density test according to the following procedure: A four inch by four inch square air laid pad having a mass of about 7.5 g is prepared from the fibers for which dry resiliency is being determined and compressed, in a dry state, by a hydraulic press to a pressure of 5000 psi and the pressure is quickly released. The pad is inverted and the pressing is repeated and released. The thickness of the pad is measured after pressing with a no-load caliper (Ames thickness tester). Five thickness readings are taken, one in the center and 0.001 inches in from each of the four corners and the five values are averaged. The pad is trimmed to 4 inches by 4 inches and then is weighed. Density after pressing is then calculated as mass/ (area×thickness). This density is denoted the 5K density herein. The lower the 5K density, the greater the fiber stiffness and the greater the dry resiliency.

The term "wet resiliency" is used herein to refer to the ability of a structure to expand upon release of compressional forces while the fibers are moistened to saturation. The wet resiliency defined by a void volume after reduction of compressional load is a measure of wet void volume and is determined herein in the "wet compressibility test" by the following procedure: An air laid four inch by four inch square pad weighing about 7.5 g is prepared from the fibers being tested. The density of the pad is adjusted to 0.2 g/cc with a press. The pad is loaded with synthetic urine to ten times its lo dry weight or to its saturation point, whichever is less. A 0.1 PSI compressional load is applied to the pad. After about 60 seconds, during which time the pad equilibrates, the compressional load is then increased to 1.1 PSI. The pad is allowed to equilibrate, and the compressional load is then reduced to 0.1 PSI. The pad is then allowed to equilibrate, and the thickness is measured. The density is calculated for the pad at the second 0.1 PSI load, i.e., based on the thickness measurement after the pad equilibrates after the compressional load is reduced to 0.1 PSI. The void volume reported in cc/g, is then determined. The void volume is the reciprocal of the wet pad density minus the fiber volume (0.95 cc/g). This void volume is denoted the wet compressibility herein. Higher values indicate greater wet responsiveness.

The drip capacity test herein provides a combined measure of absorbent capacity and absorbency rate and is carried herein by the following procedure: A four inch by four inch square air laid pad having a mass of about 7.5 g is prepared from the fibers for which drip capacity is being determined and is placed on a screen mesh. Synthetic urine is applied to the center of the pad at a rate of 8 ml/s. The flow of synthetic urine is halted when the first drop of synthetic urine escapes from the bottom or sides of the pad. The drip capacity is the difference in mass of the pad prior to and subsequent to introduction of the synthetic urine divided by the mass of the fibers, bone dry basis. The greater the drip capacity is, the better the absorbency properties.

The term "synthetic urine" is used herein to mean solution prepared from tap water and 10 grams of sodium chloride per liter of tap water and 0.51 ml of a 1.0% aqueous solution of TRITON X100, octylphenoxypolyethoxyethanol, per liter of tap water. The synthetic urine should be at 25°±1° C. when it is used.

The terms "defibration" and "defibrating" are used herein to refer to any procedure which may be used to mechanically separate fibers into substantially individual form even though they are already in such form, i.e., to the step(s) of mechanically treating fibers in either individual form or in more compacted form, where the treating (a) would separate the fibers into substantially individual form if they were not already in such form and/or (b) imparts curl to the fibers in the dry state.

DETAILED DESCRIPTION

The high lignin content fibers modified herein can be of diverse origin. Preferably, the original source is softwood or hardwood. Other sources include esparto grass, bagasse, hemp and flax and other high lignin content cellulosic fiber sources.

The high lignin content fibers which are esterified to provide the fibers used in the instant invention are, for example, chemithermomechanical pulps from the above sources, thermomechanical pulps from the above sources, and recycled fiber streams from Kraft bags and boxes where the fiber lignin content is 10% or more, on a dry basis. Unbleached cellulosic chemical pulps may also meet a 10–25% lignin content level and constitute high lignin content fibers. Chemithermomechanical pulps may be prepared in conventional fashion, e.g., by chemical treatment of source material pieces (e.g., wood chips) with, for example, sodium sulfite and/or sodium metabisulfate and a chelating agent, e.g., diethylenetriamine pentaacetic acid (DTPA) followed by processing through a disc refiner. Thermomechanical pulps may be prepared, in conventional fashion, for example, by steam treating (e.g., at conditions of 34 psi and 265° F. for 20 minutes) source material pieces (e.g., wood chips), and then processing the steam treated material through a disc refiner. Recycled fiber streams are obtained from recycled Kraft bags and boxes, e.g., by agitating them in water and then dewatering them in preparation for esterification treatment.

Northern softwood chemithermomechanical pulp is a preferred starting material since it is readily commercially available. Another starting material is Southern softwood chemithermomechanical pulp.

As used herein the term "$C_2$–$C_9$ polycarboxylic acid" refers to an aliphatic or alicyclic organic acid containing two or more carboxyl (COOH) groups and from 2 to 9 carbon atoms in the chain or ring to which the carboxyl groups are attached. The carboxyl groups are not included when determining the number of carbon atoms in the chain or ring. For example, 1,2,3 propane tricarboxylic acid would be considered to be a $C_3$ polycarboxylic acid containing three carboxyl groups. Similarly, 1,2,3,4 butane tetracarboxylic acid would be considered to be a $C_4$ polycarboxylic acid containing four carboxyl groups.

More specifically, the $C_2$–$C_9$ polycarboxylic acids suitable for use as esterifying agents to provide the esterified high lignin content cellulosic fibers of the present invention include aliphatic and alicyclic acids either saturated or olefinically unsaturated with at least three and preferably more carboxyl groups per molecule or with two carboxyl groups per molecule if a carbon-carbon double bond is present alpha, beta to one or both carboxyl groups. An additional requirement is that to be reactive in esterifying cellulose hydroxyl groups and lignin hydroxyl groups, a given carboxyl group in an aliphatic or alicyclic polycarboxylic acid must be separated from a second carboxyl group by no less than 2 carbon atoms and no more than three carbon atoms. Without being bound by theory, it appears from these requirements that for a carboxyl group to be reactive, it must be able to form a cyclic 5- or 6-membered anhydride ring with a neighboring carboxyl group in the polycarboxylic acid molecule. Where two carboxyl groups are separated by a carbon-carbon double bond or are both connected to the same ring, the two carboxyl groups must be in the cis configuration relative to each other if they are to interact in this manner. The term "reactive carboxyl group" is used herein to mean a carboxyl group separated from a second carboxyl group by no less than 2 carbon atoms and no more than 3 carbon atoms and where two carboxyl groups are separated by a carbon-carbon double bond or are both connected to the same ring, a reactive carboxyl group must be in cis configuration to another carboxyl group.

In aliphatic polycarboxylic acids containing three or more carboxyl groups per molecule, a hydroxyl group attached to a carbon atom alpha to a carboxyl group does not interfere with the esterification and crosslinking of the cellulosic fibers by the acid. Thus, polycarboxylic acids such as citric acid (also known as 2-hydroxy-1,2,3 propane tricarboxylic acid) and tartrate monosuccinic acids are suitable as esterifying agents in the present invention.

The aliphatic or alicyclic $C_2$–$C_9$ polycarboxylic acids may also contain an oxygen or sulfur atom(s) in the chain or ring to which the carboxyl groups are attached. Thus, polycarboxylic acids such as oxydisuccinic acid also known as 2,2'-oxybis(butanedioic acid), thiodisuccinic acid, and the like, are meant to be included within the scope of the invention. For purposes of the present invention, oxydisuccinic acid would be considered to be a $C_4$ polycarboxylic acid containing four carboxyl groups.

Examples of specific polycarboxylic acids suitable for use to provide the esterified high lignin content cellulosic fibers of this invention include the following: maleic acid, citraconic acid also known as methylmaleic acid, citric acid, itaconic acid also known as methylenesuccinic acid, tricarballylic acid also known as 1,2,3 propane tricarboxylic acid, transaconitic acid also known as trans-1-propene-1,2,3-tricarboxylic acid, 1,2,3,4-butanetetracarboxylic acid, all-cis-1,1,3,4-cyclopentanetetracarboxylic acid, mellitic acid also known as benzenehexacarboxylic acid, and oxydisuccinic acid also known as 2,2'-oxybis(butanedioic acid). The above list of specific polycarboxylic acids is for exemplary purposes only, and is not intended to be all inclusive. Importantly, the esterifying agent must be capable of reacting with at least two hydroxyl groups on proximately located cellulose chains in a single cellulosic fiber.

Preferably, the $C_2$–$C_9$ polycarboxylic acids used to provide the esterified high lignin content cellulosic fibers herein are aliphatic, and saturated, and contain at least three carboxyl groups per molecule. One group of preferred polycarboxylic acid agents for use to provide the esterified high lignin content cellulosic fibers of the present invention includes citric acid also known as 2-hydroxy-1,2,3 propane tricarboxylic acid, 1,2,3 propane tricarboxylic acid, and 1,2,3,4 butane tetracarboxylic acid. Citric acid is especially preferred, since it has provided fibers with high levels of wettability, absorbency and resiliency, which are safe and non-irritating to human skin, and has provided stable, crosslink bonds. Furthermore, citric acid is available in large quantities at relatively low prices, thereby making it commercially feasible for use as the esterifying agent.

Another group of preferred esterifying agents for use to provide the esterified high lignin content cellulosic fibers of the present invention includes saturated $C_2$–$C_9$ polycarboxylic acids containing at least one oxygen atom in the chain to which the carboxyl groups are attached. Examples of such compounds include oxydisuccinic acid, tartrate monosuccinic acid having the structural formula:

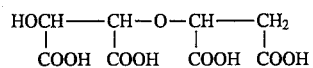

and tartrate disuccinic acid having the structural formula:

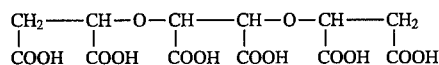

A more detailed description of tartrate monosuccinic acid, tartrate disuccinic acid, and salts thereof, can be found in Bushe et al U.S. Pat. No. 4,663,071, issued May 5, 1987, incorporated herein by reference.

Those knowledgeable in the area of polycarboxylic acids will recognize that the aliphatic and alicyclic $C_2$–$C_9$ polycarboxylic acid esterifying agents described above may be reacted in a variety of forms to provide the esterified high lignin content cellulosic fibers herein, such as the free acid form, and salts thereof. Although the free acid form is preferred, all such forms are meant to be included within the scope of the invention.

The individualized, esterified fibers of the instant invention have an effective amount of esterifying acid reacted therewith in the form of intrafiber ester moieties, i.e., an amount which provides improvement (i.e., increase) in stiffness (dry resiliency 5K density values as indicated above). This normally ranges from about 0.5 to about 8%, preferably from 3 to 4.5%, by weight on a citric acid applied on a dry fiber basis, of reacted $C_2$–$C_9$ polycarboxylic acid.

We turn now to methods for preparing the individualized esterified high lignin content cellulosic fibers.

Initially the high lignin content fibers to be esterified are contacted with polycarboxylic acid esterifying agent sufficiently to allow uniform penetration and distribution of the acid onto the fibers. This is preferably achieved by contacting the fibers with the esterifying acid in a liquid medium, e.g., an aqueous esterifying composition.

The pH of the aqueous esterifying composition applied can be, for example, 1 to 5.0. The pH's below I are corrosive to the processing equipment. The pHs above 5.0 provide an impractically low reaction rate. The esterification reaction will not occur at alkaline pH. Increasing pH reduces reaction rate. The pH preferably ranges from 1.5 to 3.5. The pH is readily adjusted upward if necessary by addition of base, e.g., sodium hydroxide.

Catalyst is preferably included in the aqueous esterifying composition applied, to speed up the crosslinking reaction and protect brightness. The catalyst can be any which catalyzes the esterification reactions. Applicable catalysts include, for example, alkali metal hypophosphites, alkali metal phosphites, alkali metal polyphosphates, alkali metal phosphates, and alkali metal sulfates. Especially preferred catalysts are the alkali metal hypophosphites, alkali metal phosphites, and alkali metal sulfates. The mechanism of the catalysis is unknown, although the catalysts may simply be functioning as buffering agents, keeping the pH levels within the desired ranges. A more complete list of catalysts useful ,/herein can be found in Welch et al U.S. Pat. No. 4,820,307, issued April 1989, incorporated herein by reference. The selected catalyst may be utilized as the sole catalyzing agent, or in combination with one or more other catalysts. The amount of catalyst preferably utilized is, of course, dependent upon the particular type and amount of esterifying agent, the pH and the curing conditions (as described hereinafter), especially temperature. In general, based upon technical and economic considerations, catalyst levels of between about 5 wt. % and about 80 wt. %, based on the weight of esterifying agent added to the cellulosic fibers, are preferred. For exemplary purposes, in the case wherein the catalyst utilized is sodium hypophosphite and the esterifying agent is citric acid, a catalyst level of about 25 wt. %, based upon the amount of citric acid added, is preferred.

The polycarboxylic acid esterifying agent is normally used in an amount to provide on the fibers subjected to curing (as described hereinafter) from I to 15%, preferably from 3 to 12%, thereof, on a citric acid basis applied on a dry fiber basis. The higher-the amount used, the greater the amount of ester moieties obtained and the greater the fiber stiffness and dry and wet resiliency obtained.

The esterification reactions are caused to occur in a curing step. This should preferably be carried out to obtain the substantial absence of interfiber bonds. The substantial absence of interfiber bonds is fostered by fluffing (i.e., defibrating) to maintain interfiber contact in a low degree of occurrence relative to unfluffed fibers prior to curing or by carrying out the curing while the fibers are submerged in a liquid.

Defibration is preferably performed by a method wherein knot and pill formation and fiber damage are minimized. Typically, a commercially available disc refiner is used. Another type of device which has been found to be particularly useful for defibrating the cellulosic fibers is the three stage fluffing device described in U.S. Pat. No. 3,987,968, issued to D. R. Moore and O. A. Shields on Oct. 26, 1976, said patent being hereby expressly incorporated by reference into this disclosure. The fluffing device described in U.S. Pat. No. 3,987,968 subjects moist cellulosic pulp fibers to a combination of mechanical impact, mechanical agitation, air agitation and a limited amount of air drying to create a substantially knot-free fluff. Other applicable methods of defibration include, but are not limited to, treatment in a Waring blender, tangentially contacting the fibers with a wire brush and hammermilling. Preferably, an air stream is directed toward the fibers during such defibration to aid in separating the fibers into substantially individual form. Regardless of the particular mechanical device used to form the fluff, the fibers are preferably mechanically treated while initially containing at least about 20% moisture content, and normally containing between about 40% to 70% moisture content. Lower consistencies detract from aesthetic appearance (result in knots and pills). Too high a consistency detracts from performance resulting in and less absorbency in absorbent structures.

The esterified fibers herein are preferably prepared by a method involving dry curing. They may also be prepared in a method involving a non-aqueous solution cure.

We turn firstly to the dry curing methods. These involve introducing the fibers into the curing stage when they are at consistency of at least 60%, preferably when they are at a consistency of at least 90%.

One method for preparing the esterified fibers herein involving dry curing normally comprises the steps of contacting unesterified fibers with aqueous esterifying composition so as to obtain uniform penetration and distribution of esterifying composition thereon, optionally dewatering, optionally drying further, optionally defibrating the fibers into substantially individual form, a heating step to remove any moisture content and to cause the esterification reactions to occur (i.e., to cause curing), optionally washing or optionally bleaching and washing.

The steps prior to curing (in the heating step) are normally carried out to provide on the fibers subjected to curing, from 1 to 15%, preferably from 3 to 12%, by weight on a citric acid basis applied on a dry fiber basis, of the $C_2$-$C_9$ polycarboxylic acid.

In a very preferred method of producing the individualized esterified high lignin content cellulosic fibers herein, said contacting is carried out by transporting a sheet of uncrosslinked high lignin content cellulosic fibers having a moisture content ranging from 0 to 10% through a body of said aqueous esterifying composition contained in a nip of press rolls (e.g., rolls 1 foot in diameter and 6 feet wide) and through said nip to impregnate said sheet of fibers with said aqueous crosslinking composition and to produce on the outlet side of the nip an impregnated sheet of fibers containing said aqueous crosslinking composition in an amount providing 30 to 80% or more (e.g., even up to 85% or 90% or even 95%), preferably 40 to 70%, consistency, and the impregnated sheet of fibers is subjected to defibration to produce a defibrated admixture which is ready for treatment in said heating step to cause moisture removal and curing. The time of the sheet of fibers in the body of aqueous crosslinking composition as determined by the rotation speed of the press rolls, and the pressure of the rolls on the sheet of fibers passing therethrough, are regulated so that the appropriate consistency and amount of crosslinking composition as specified above, are obtained. The press roll speed is normally regulated to provide a time of the sheet of uncrosslinked fibers in the aqueous crosslinking composition ranging from 0.005 to 60 seconds, preferably, from 0.05 to 5 seconds. In a less preferred alternative, the sheet of uncrosslinked cellulosic fibers is impregnated with aqueous esterifying to provide the aforementioned consistencies by spraying. In either case, the moisture content of the sheet is optionally adjusted prior to defibrating by mechanically pressing and/or by air drying. In examples of this method, a sheet of fibers of 6% moisture content is transported through a body of aqueous crosslinking composition to produce on the outlet side of the press rolls an impregnated sheet of fibers of 60% consistency or 80% consistency which is subjected to difibration or an impregnated sheet of fibers of 40% consistency which is air dried to 60% consistency and then is subjected to defibration.

In another method of producing the individualized esterified high lignin content cellulosic fibers herein, the contacting is carried out by forming a slurry of uncrosslinked high lignin content cellulosic fibers in unrestrained form in the aqueous esterifying composition, of 0.1 to 20%, very preferably from 2 to 15%, consistency, and soaking for about 1 to 240 minutes, preferably for 5 to 60 minutes, whereupon liquid is removed from the slurry to increase the consistency to range from 30 to 100% to form a liquid-reduced admixture, whereupon the liquid-reduced admixture is subjected to defibration to form a defibrated admixture which is ready for treatment in said heating step. The liquid removal is typically carried out by removing liquid to provide a consistency ranging from about 30 to 80%, preferably ranging from about 40 to 50%, by mechanically pressing or centrifuging and then drying under conditions such that utilization of high temperature for an extended period of time is not required, e.g., by a method known in the art as air drying, typically to provide a consistency within a 35 to 80% consistency range, preferably to provide a consistency ranging from 50 to 70%.

We turn now to the heating step.

In the case of treating fibers in unrestrained form, e.g., defibrated (fluffed) admixture, an initial moisture content removal portion of the heating step may be carried out in separate apparatus to dry to a consistency ranging from 60% to 100%, e.g., 90%, by a method known in the art as flash drying. This is carried out by transporting the fibers in a hot air stream at an introductory air temperature ranging from 200° to 750° F., preferably at an introductory air temperature ranging from 300° to 550° F., until the target consistency is reached. This imparts additional curl to the fibers as water is removed from them. While the amount of water removed by this additional drying step may be varied, it is believed that flash drying to the higher consistencies in the 60% to 100% range provides a greater level of fiber curl than does flash drying to a consistency in the low part of the 60%–100% range. In the preferred embodiments, the fibers are dried to about 85%–95% consistency. Flash drying the fibers to a consistency, such as 85%–95%, in a higher portion of the 60%–100% range reduces the amount of drying which must be accomplished following flash drying. The subsequent portion of the heating step, or all of the heating step if flash drying is omitted, can involve heating for a period ranging from 5 seconds to 2 hours at a temperature ranging from 120° C. to 280° C. (air temperature in the heating apparatus), preferably at a temperature ranging from 145° to 190° C. (air temperature in the heating apparatus) for a period ranging from 2 minutes to 60 minutes, in continuous air-through drying/curing apparatus (heated air is passed perpendicularly through a traveling bed of fibers) or in a static oven (fibers and air maintained stationary in a container housing a stationary heating means), or other heating apparatus, to remove any remaining moisture content and to cause esterification reactions (i.e., curing) to occur which stiffen the fibers as a result of intrafiber crosslinking. The heating should be such that the temperature of the fibers does not exceed about 227° C. (440° F.) since the fibers can burst into flame at this temperature. The admixture is heated for an effective period of time to remove any remaining moisture content and to cause the esterifying agent to react with the cellulosic fibers. The extent of reaction depends upon the dryness of the fiber, the time in the heating apparatus, the air temperature in the heating apparatus, pH, amount of catalyst and esterifying agent and the method used for heating. Esterifying at a particular temperature will occur at a higher rate for fibers of a certain initial moisture content with continuous, air-through drying/curing than with drying/curing in a static oven. Those skilled in the art will recognize that a number of temperature-time relationships exist. Temperatures from about 145 ° C. to about 165 ° C. (air temperature in the heating apparatus) for periods between about 30 minutes and 60 minutes, under static atmosphere conditions will generally provide acceptable drying/curing efficiencies for fibers having moisture contents less than about 10%. Those skilled in the art will also appreciate that higher temperatures and forced air convection (air-through heating) decrease the time required. Thus, temperatures ranging from about 170° C. to about 190° C. (air temperature in the heating apparatus) for periods between about 2 minutes and 20 minutes, in an airthrough oven will also generally provide acceptable drying/curing efficiencies for fibers having moisture contents less than 10%. In an alternative for completing the heating after an initial flash drying step, flash drying and curing are carried out, or curing only is carried out if the effluent from the prior flash drying has a consistency of 100%, by routing the effluent from the flash drier (at 90 to 100% consistency) to a cyclone separator which separates air from the air/fiber admixture from the flash drier, discharging the fibers from the cyclone separator into a stream of hot air (e.g., 400° F.) in a duct containing at least one U-shaped portion, which carries the fibers through the duct thereby providing a travel path which provides sufficient residence time to cause removal of any moisture content and to cause esterification reaction to occur between fibers and the $C_2$–$C_9$ polycarboxylic acid, and discharging from the duct into a cyclone separator to separate the esterified fibers, and if necessary or desired, causing additional crosslinking to occur, e.g., in a subsequent air-through oven or static oven. Apparatus for the initial flash drying step may also be the same kind of apparatus as described for the alternative for completing the heating (an inlet side cyclone separator, hot air treatment duct and discharge side cyclone separator), so that two or more sets of such apparatus are used in series as required by the need to bring in fresh dry air over the course of drying and curing.

We turn now to the optional washing step. The function of this is to remove excess, unreacted esterifying agent and catalyst.

One series of treatments found to successfully remove excess esterifying agent comprise, in sequence, allowing the fibers to soak in an aqueous washing solution for an appreciable time, e.g., 30 minutes to 1 hour, screening the fibers, dewatering the fibers, e.g., by centrifuging, to a consistency of between about 50% and about 80%, optionally mechanically defibrating the dewatered fibers as previously described and air drying the fibers. A sufficient amount of an acidic substance may be added to the wash solution, if necessary, to keep the wash solution at a pH of less than about 7. Without being bound by theory, it is believed that the ester moieties are not stable under alkaline conditions and that keeping the wash treatment pH in the acidic range inhibits reversion of the ester moieties which have formed.

We turn now to a second method for preparing the esterified fibers herein, which involves dry curing. In this method, the unesterified cellulosic fibers are contacted with an aqueous solution containing esterifying agent as described above. Either before or after being contacted with the esterifying agent, the unesterified fibers are provided in sheet form. The fibers, while in sheet form, are dried and cured (to cause the esterification reactions to occur), preferably by heating at about 145° to about 190° C. (air temperature in the heating apparatus). The esterified fibers are optionally defibrated into substantially individual form, preferably by treating with a commercially available disc refiner. The esterified fibers made by this method would be expected to exhibit lower dry and wet resiliency than the esterified fibers made by the first described method. In a particular embodiment of this method a sheet of fibers impregnated with aqueous esterifying composition is prepared as described above and the impregnated sheet of fibers is dried and cured (i.e., without prior defibrating) and is optionally subjected to defibrating after curing.

We turn now to a method for forming the esterified cellulosic fibers herein involving a non-aqueous solution cure. The same conditions apply as in the dry curing processes described above prior to curing (i.e., reaction of the fibers with $C_2$–$C_9$ polycarboxylic acid). For curing, however, the esterifying agent is caused to react while the fibers are submerged in a substantially nonaqueous solution. The nonaqueous esterification solution contains a nonaqueous, water-miscible, polar diluent such as, but not limited to, acetic acid, propanoic acid, or acetone. The esterification solution may also contain a limited amount of water or other fiber swelling liquid; however, the amount of water is preferably insufficient to induce any substantial levels of fiber swelling.

The esterified high lignin content cellulosic fibers herein can be unbleached or partially bleached or completely bleached. Bleaching provides the advantages of superior brightness and consumer appeal. A problem involved in bleaching esterified high lignin content cellulosic fibers is that it can remove ester crosslinks which are vital to the advantageous resiliency, and absorbency properties. Thus, to preserve the advantages of the inventions herein, a bleaching process for the esterified high lignin content cellulosic fibers herein comprises bleaching using an acidifying and nondelignifying bleaching agent, such as peracetic acid, removing residual bleaching agent, e.g., by centrifuging and then washing by soaking in or rinsing with water, then dewatering, e.g., by centrifuging, optionally defibrating, and drying, e.g., in an air-through drier.

The resulting esterified fibers (produced by any of the methods described above, whether bleached or unbleached, are optionally moisturized, e.g., by spraying with water to provide 5 to 15% moisture content. This makes the fibers resistant to damage that is of risk to occur due to subsequent handling or due to processing in making absorbent products from the fibers.

We turn now to the uses of the esterified high lignin content cellulosic fibers herein.

The esterified fibers herein are also useful, for example, for a variety of absorbent structures including, but not limited to, paper towels, tissue sheets, disposable diapers, training pants, catamenials, sanitary napkins, tampons, and bandages wherein each of said articles has an absorbent structure containing the individualized, esterified fibers described herein. For example, a disposable diaper or similar article having a liquid permeable topsheet, a liquid impermeable backsheet connected to the topsheet, and an absorbent structure containing the individualized, esterified fibers herein is particularly contemplated. Such articles are described generally in U.S. Pat. No. 3,860,003, issued to Kenneth B. Buell on Jan. 14, 1975, hereby incorporated by reference into this disclosure.

The esterified fibers herein used in the absorbent structures of the present invention are preferably prepared by the dry curing process discussed above where curing is carried out on the fibers in individual form. The esterified fibers herein may be utilized directly in the manufacture of air laid absorbent cores. Additionally, due to their stiffened and resilient character, the esterified fibers herein may be wet laid into an uncompacted, low density sheet which, when subsequently dried, is directly useful without further mechanical processing as an absorbent core. The esterified fibers herein may also be wet laid as compacted pulp sheets for sale or transport to distant locations.

Relative to pulp sheets made from conventional cellulosic fibers, the pulp sheets made from the esterified fibers of the present invention, are more difficult to compress to conventional pulp sheet densities. Therefore, it may be desirable to combine the fibers herein with conventional fibers, such as those conventionally used in the manufacture of absorbent cores. Pulp sheets containing stiffened fibers preferably contain between about 5% and about 90% uncrosslinked, cellulosic fibers, based upon the total dry weight of the sheet, mixed with the individualized, esterified fibers of the invention herein. It is especially preferred to include between about 5% and about 30% of highly refined, uncrosslinked cellulosic fibers, based upon the total dry weight of the sheet. Such highly refined fibers are refined or beaten to a freeness level less than about 300 ml CSF, and preferably less than 100 ml CSF. The uncrosslinked fibers are preferably mixed with an aqueous slurry of the individualized, esterified fibers of the invention herein. This mixture may then be formed into a densified pulp sheet for subsequent defibration and formation into absorbent pads. The incorporation of the uncrosslinked fibers eases compression of the pulp sheet into a densified form, while imparting a surprisingly small loss in absorbency to the subsequently formed absorbent pads. The uncrosslinked fibers additionally increase the tensile strength of the pulp sheet and of absorbent pads made either from the pulp sheet or directly from the mixture of the fibers herein and uncrosslinked fibers. Regardless of whether the blend of the fibers herein and uncrosslinked fibers are first made into a pulp sheet and then formed into an absorbent pad or formed directly into an absorbent pad, the absorbent pad may be air laid or wet-laid.

Sheets or webs made from the individualized, esterified fibers herein, or from mixtures also containing uncrosslinked fibers, will preferably have basis weights of less than about 800 g/m$^2$ and densities of less than about 0.60 g/cm$^3$. Although it is not intended to limit the scope of the invention, wet-laid sheets having basis weights between 300 g/m$^2$ and about 600 g/m$^2$ and densities between 0.07 g/cm$^3$ and about 0.30 g/cm$^3$ are especially contemplated for direct application as absorbent cores in disposable articles such as diapers, tampons, and other catamenial products. Structures having basis weights and densities higher than these levels are believed to be most useful for subsequent comminution and air-laying or wet-laying to form a lower density and basis weight structure which is more useful for absorbent applications. Such higher basis weight and density structures also exhibit surprisingly high absorptivity and responsiveness to wetting. Other absorbent structure applications contemplated for the fibers of the present invention include low density tissue sheets having densities which may be less than about 0.03 g/cc.

In one application to absorbent structures, the individualized, esterified fibers herein are formed into either an air laid or wet laid (and subsequently dried) absorbent core which is compressed to pad form to a dry density less than the equilibrium wet density of the pad. The equilibrium wet density is the density of the pad, calculated on a dry fiber basis when the pad is fully saturated with fluid. When fibers are formed into an absorbent core having a dry density less than the equilibrium wet density, upon wetting to saturation, the core will collapse to the equilibrium wet density. Alternatively, when fibers are formed into an absorbent core having a dry density greater than the equilibrium wet density, upon wetting to saturation, the core will expand to the equilibrium wet density. Pads made from the fibers of the present invention have equilibrium wet densities which are substantially lower than pads made from conventional fluffed fibers. The fibers of the present invention can be compressed to a density higher than the equilibrium wet density, to form a thin pad which, upon wetting, will expand, thereby increasing absorbent capacity, to a degree significantly greater than obtained for uncrosslinked fibers.

Absorbent structures made from individualized, esterified fibers herein may additionally contain discrete particles of substantially water-insoluble, hydrogel-forming materials. Hydrogel-forming materials are chemical compounds capable of absorbing fluids and retaining them under moderate pressures.

Suitable hydrogel-forming materials can be inorganic materials such as silica gels or organic compounds such as crosslinked polymers. It should be understood that crosslinking, when referred to in connection with hydrogel forming materials, assumes a broader meaning than contemplated in connection with the reaction of esterifying agents with cellulosic fibers to form individualized, esterified fibers herein. Crosslinked hydrogel-forming polymers may be crosslinked by covalent, ionic, Van der Waals, or hydrogen bonding. Examples of hydrogel-forming materials include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogel-forming materials are those disclosed in Assarsson et al, U.S. Pat. No. 3,901,236, issued Aug. 26, 1975, the disclosure of which is incorporated herein by reference. Particularly preferred hydrogel-forming polymers for use in an absorbent core herein are hydrolyzed acrylonitrile grafted starch, acrylic acid grafted starch, polyacrylates, and isobutylene maleic anhydride copolymers, or mixtures thereof. Examples of hydrogel-forming materials which may be used are Aqualic L-73, a partially neutralized polyacrylic acid made by Nippon Shokubai Co., Japan, and Sanwet IM 1000, a partially neutralized polyacrylic acid grafted starch made by Sanyo Co., Ltd., Japan. Hydrogel forming materials having relatively/high gel strengths, as are preferably mixed with an aqueous slurry of the described in U.S. Pat. No. 4,654,039, issued Mar. 31, 1987, hereby incorporated herein by reference, are preferred for utilization with individualized esterified fibers herein.

Process for preparing hydrogel-forming materials are disclosed in Masuda et al, U.S. Pat. No. 4,076,663, issued Feb. 28, 1978; in Tsubakimoto et al, U.S. Pat. No. 4,286,082, issued Aug. 25, 1981; and further in U.S. Pat. Nos. 3,734, 876, 3,661,815, 3,670,731, 3,664,343, 3,783,871, the disclosures of which are all incorporated herein by reference.

The hydrogel-forming material may be distributed throughout an absorbent structure containing individualized, esterified fibers, or be limited to distribution throughout a particular layer or section of the absorbent structure. In another embodiment, the hydrogel-forming material is adhered or laminated onto a sheet or film which is juxtaposed against a fibrous, absorbent structure, which may include individualized, crosslinked fibers. Such sheet or film may be multilayered such that the hydrogel-forming material is contained between the layers. In another embodiment, the hydrogel-forming material may be adhered directly onto the surface fibers of the absorbent structure.

An important advantage has been observed with respect to absorbent structures made from individualized, esterified fibers herein having dry densities which are higher than their corresponding equilibrium wet densities (calculated on a dry fiber basis). Specifically, this type of absorbent structure expands in volume upon wetting. As a result of this expansion, the interfiber capillary network of fibers also enlarges. In conventional absorbent structures having hydrogel-forming material blended therein, the hydrogel-forming material expands in volume due to fluid absorption, and may block or reduce in size the capillary routes for fluid absorption prior to utilization of the entire fluid absorbing potential of the structure. This phenomenon is known as gel blocking. Capillary enlargement due to expansion of fibrous network of absorbent structure utilizing the individualized esterified fibers herein reduces the occurrence of gel blocking. This allows larger proportions of the fluid absorbency potential of the structure to be utilized and allows higher levels of hydrogel-forming material (if desired) to be incorporated into the absorbent structure, without significant levels of gel-blocking.

Absorbent structures containing the individualized, esterified fibers herein and hydrogel-forming material for diaper core applications preferably have dry densities of between about 0.15 g/cc and about 0.40 g/cc and preferably contain less than about 20% hydrogel-forming material, calculated on a dry fiber weight basis.

The hydrogel-forming material may be homogeneously dispersed throughout all or part of the absorbent structure. For a diaper structure as disclosed in U.S. Pat. No. 3,860,003 having an absorbent core which contains the preferred individualized, esterified fibers herein, has a dry density of about 0.20 g/cc, and also contains hydrogel-forming material dispersed throughout the core, it is presently believed that an optimal balance of diaper wicking, total absorbent capacity, skin wetness, and economic viability is obtained for contents of between about 5 wt. % and about 20 wt. %, based on the total weight of the dry absorbent core, of a hydrogen forming material such as Aqualic L-73. Between about 8 wt. % and about 10 wt. % of hydrogel-forming material is preferably homogeneously blended with the individualized, esterified fiber-containing absorbent cores in products as disclosed in U.S. Pat. No. 3,860,003.

The absorbent structures described above may also include conventional, fluffed fibers, or highly refined fibers, wherein the amount of hydrogel-forming material is based upon the total weight of the fibers as previously discussed. The embodiments disclosed herein are exemplary in nature and are not meant to limit the scope of application of hydrogel-forming materials with individualized, esterified fibers.

The invention herein is illustrated by the following specific examples.

In examples and reference examples hereinafter, results are evaluated in terms of WRV, 5K density, drip capacity, and wet compressibility.

REFERENCE EXAMPLE 1

Drylap sheets of market Northern softwood chemithermomechanical pulp (CTMP) fibers (Sphinx), having about 20% lignin content, were dispersed by dipping and mixing with a paddle wheel mixer in a solution of citric acid and water at pH of 3.0 to yield a 10% consistency mixture. Soaking was then carried out for about 30 minutes. The resulting mixture was centrifuged to provide a dewatered cake of approximate consistency of 50%. The dewatered cake, containing 6% by weight citric acid on a fiber basis, was air dried to about 60% consistency, fluffed in a lab disk refiner and flash dried to about 90% consistency. Testing indicated a WRV of 131, a 5K density of 0.235 g/cc, a drip capacity of 5.9 g/g, and a wet compressibility at of 7.0 cc/g.

REFERENCE EXAMPLE II

Esterified fibers were prepared from Northern softwood Kraft pulp (lignin content about 5%) using citric acid as esterifying agent. In the preparation, admixture was formed of the Northern softwood Kraft fibers and citric acid at a pH of 3.0 to yield a 10% consistency mixture. Soaking was then carried out for about 30 minutes. The resulting mixture was centrifuged to an approximate consistency of 50%. The resultant dewatered fiber cake contained 6% by weight citric acid on a fiber basis. The fiber cake was air dried to about 60% consistency, fluffed in a lab disc refiner, flash dried to about 90% consistency, and then heated for 60 minutes at an air temperature of 165° C. and washed. Testing indicated a WRV of 35, a 5K density of 0.14 g/cc, a drip capacity of 7.0 g/g and a wet compressibility of 7.0 cc/g.

REFERENCE EXAMPLE III

Esterified fibers were prepared from Southern softwood Kraft pulp (lignin content about 5%) using citric acid as the esterifying agent. In the preparation, admixture was formed of the Southern softwood Kraft fibers and citric acid at a pH of 3.0 to yield a 10% consistency mixture. Soaking was then carried out for about 30 minutes. The resulting mixture was centrifuged to an approximate consistency of 50%. The resultant dewatered fiber cake contained 6% by weight citric acid on a fiber basis. The fiber cake was air dried to about 60% consistency, flash dried to about 90% consistency, fluffed in a lab disc refiner and then heated for 60 minutes at an air temperature of 165° C. Testing indicated a WRV of 35, a 5K density of 0.120 g/cc, a drip capacity of 14.7 g/g, and a wet compressibility of 7.4 cc/g.

EXAMPLE 1

Processing was carried out as in Reference Example I except that the flash dried CTMP fibers were dried and cured in a laboratory oven at an air temperature of 165° C. for about 20 minutes. Testing indicated a WRV of 93, a 5K density of 0.135 g/cc, a drip capacity of 10.2 g/g, and a wet compressibility 8.5 cc/g. The improvement in wet compressibility in comparison to that obtained in Reference Example I is considered to be a surprising improvement. Similar results are obtained when an equivalent amount of tetracarboxylic acid (in the dewatered cake) or oxydisuccinic acid (in the dewatered cake) is substituted for the citric acid.

EXAMPLE II

Processing was carried out as in Example I except that the esterified fibers were prepared from Southern softwood chemithermomechanical pulp (lignin content of about 20%), centrifuging was carried out to provide a consistency of about 44%, air drying was carried out to provide a consistency of about 48% and heating was carried out in an air-through oven for 2 minutes at an air temperature of 307° F. The dewatered fiber cake obtained from centrifuging contained 6% by weight citric acid on a fiber basis. Testing indicated a 5K density of 0.16 g/cc, a drip capacity of 12.4 g/g and a wet compressibility of 8.3 cc/g. The WRV was not measured but is estimated to be within the range of 65 to 125. The improvement in wet compressibility in comparison to that obtained in Reference Example III is considered to be a surprising improvement.

EXAMPLE III

Individualized esterified fibers prepared as in Example I are air laid into absorbent pads, and compressed with a hydraulic press to a density of about 0.1 g/cc and a basis weight of about 0.13 g/in$^2$. The pad is cut to 15" by 3" for use as an absorbent pad for a sanitary napkin.

Variations will be obvious to those skilled in the art. Therefore, the invention is defined by the scope of the claims.

What is claimed is:

1. An absorbent structure comprising individualized esterified high lignin content cellulosic fibers containing from about 0.5 to 8% by weight, on a citric acid basis applied on a dry fiber basis, of reacted $C_2$–$C_9$ polycarboxylic acid and having a water retention value ranging from about 65 to 125, a dry resiliency defined by a 5K density ranging from about 0.08 to 0.22 gm/cc, a wet resiliency defined by a wet compressibility ranging from about 6.0 to 11.0 cc/gm and a drip capacity ranging from about 7.0 to 16.0 g/g.

2. The absorbent structure of claim 1 wherein said polycarboxylic acid is citric acid.

3. The absorbent structure of claim 1 wherein said fibers have a water retention value ranging from about 75 to 110, a dry resiliency defined by a 5K density ranging from about 0.10 to 0.18 gm/cc, a wet resiliency defined by a wet compressibility ranging from about 7.2 to 8.75 cc/gm and a drip capacity ranging from about 8.0 to 12.5 g/g.

4. The absorbent structure of claim 1 wherein the high lignin content fibers which are esterified are Northern softwood chemithermomechanical pulp fibers.

5. The absorbent structure of claim 1 wherein the high lignin content fibers which are esterified are Southern softwood chemithermomechanical pulp fibers.

6. The absorbent structure of claim 1 further comprising a hydrogel-forming material disposed within said absorbent structure.

7. The absorbent structure of claim 1 wherein said absorbent structure has a basis weight of less than about 800 g/m$^2$ and a density of less than about 0.60 g/cm$^3$.

8. The absorbent structure of claim 3 wherein said individualized high lignin content cellulosic fibers contain from about 3% to about 4.5% by weight, on a citric acid basis applied on a dry fiber basis, of reacted $C_2$–$C_9$ polycarboxylic acid.

9. Individualized esterified cellulosic fibers containing about 10 to 25% by weight lignin, on a dry basis, and containing from about 0.5 to 8% by weight, on a citric acid basis applied on a dry fiber basis, of reacted $C_2$–$C_9$ polycarboxylic acid and having a water retention value ranging from about 75 to 110, a dry resiliency defined by a 5K density ranging from about 0.10 to 0.18 gm/cc, a wet resiliency defined by a wet compressibility ranging from about 7.2 to 8.75 cc/gm and a capacity ranging from about 8.0 to 12.5 g/g.

10. The individualized esterified cellulosic fibers of claim 9 wherein the polycarboxylic acid is citric acid.

11. The individualized esterified cellulosic fibers of claim 9 wherein the fibers which are esterified are Northern softwood chemithermomechanical pulp fibers.

12. The individualized esterified cellulosic fibers of claim 9 wherein the fibers which are esterified are Southern softwood chemithermomechanical pulp fibers.

\* \* \* \* \*